United States Patent
Kazakov et al.

(10) Patent No.: US 6,623,483 B1
(45) Date of Patent: Sep. 23, 2003

(54) APPARATUS FOR TRANSOSSEOUS OSTEOSYNTHESIS

(75) Inventors: Mark Evgenievich Kazakov, Moscow (RU); Vladislav Markovich Kernichansky, Mytischi (RU)

(73) Assignee: Obschestvo S Ogranichennoi Otvetstvennostiju Nauchno-Proizvodstvenny Tsentr "Uglerodnye Volokna I Kompozity", Moskovskaya (RU)

( * ) Notice: Subject to any disclaimer, the term of this patent is extended or adjusted under 35 U.S.C. 154(b) by 0 days.

(21) Appl. No.: 10/168,577
(22) PCT Filed: Sep. 22, 2000
(86) PCT No.: PCT/RU00/00381
§ 371 (c)(1),
(2), (4) Date: Jun. 21, 2002
(87) PCT Pub. No.: WO01/45575
PCT Pub. Date: Jun. 28, 2001

(30) Foreign Application Priority Data

Dec. 21, 1999 (RU) .......................................... 99127399
Jun. 19, 2000 (RU) ........................................ 2000116234

(51) Int. Cl.$^7$ ............................................... A61B 17/66
(52) U.S. Cl. .......................................... 606/57; 606/59
(58) Field of Search ............................. 606/54, 57, 58, 606/59

(56) References Cited

U.S. PATENT DOCUMENTS

| | | | | |
|---|---|---|---|---|
| 1,789,060 A | * | 1/1931 | Weisenbach | |
| 4,360,012 A | * | 11/1982 | McHarrie et al. | 128/92 |
| 4,564,007 A | * | 1/1986 | Coombs et al. | 128/92 |
| 4,584,995 A | * | 4/1986 | Koeneman | 128/92 |
| 4,745,913 A | | 5/1988 | Castaman et al. | |

FOREIGN PATENT DOCUMENTS

| | | |
|---|---|---|
| RU | 1806660 | 4/1993 |
| RU | 2125417 | 1/1999 |
| RU | 2125418 | 1/1999 |

\* cited by examiner

*Primary Examiner*—Eduardo C. Robert
*Assistant Examiner*—Anuradha Ramana
(74) *Attorney, Agent, or Firm*—Ladas & Parry

(57) ABSTRACT

The inventive apparatus for transosseous osteosynthesis comprises a detachable repositioning mechanism for axial compression and distraction of bone fragments, the mechanism having a thrust element with two guiding bars. A mobile traverse is mounted on the guiding bars. A lead screw which interacts with a screw orifice of the mobile traverse is fixed in the thrust element. Two side bars for movement of bracing frames, one end of each of the side bars being fixed to the mobile traverse, the other end being fixed to a holder with the aid of a screw clamp. The apparatus has at least two holders, each comprising a hollow body with an inner cylindrical surface, the axis of the body coincides with the axis of a corresponding tightening bolt, and also has a stem on the side surface of the body with an opening, which stem has a threaded portion. A latch is disposed in the holder body and is intended for fixing the holder in the direction of axial movement along the tightening bolt. According to another embodiment, the apparatus comprises an assembly for drawing in and fixing the bone fragments, which assembly is disposed between the strips having longitudinal slots.

9 Claims, 4 Drawing Sheets

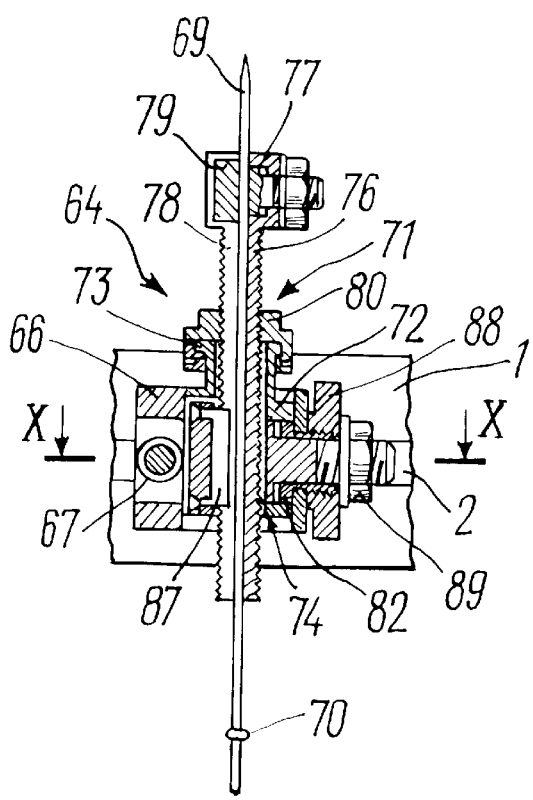
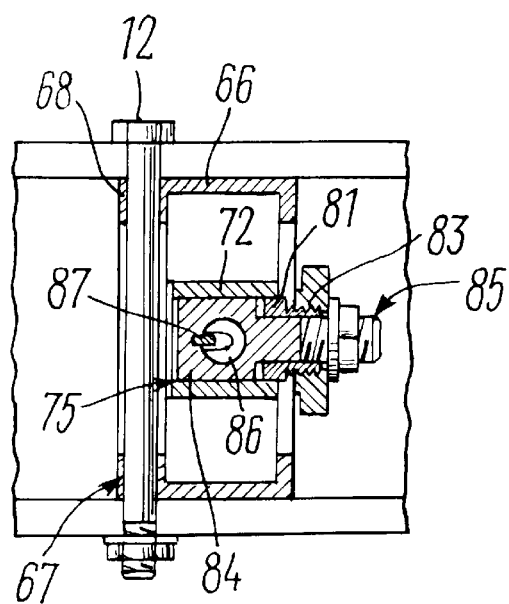
FIG. 9
FIG. 10

APPARATUS FOR TRANSOSSEOUS OSTEOSYNTHESIS

FIELD OF THE INVENTION

The invention relates to medical engineering in the field of traumatology and orthopedics, particularly—to an apparatus for transosseous osteosynthesis.

BACKGROUND OF THE INVENTION

Known is an apparatus for transosseous osteosynthesis, which apparatus, in order to provide graduated compression and distraction of bone fragments, comprises a detachable repositioning mechanism made in the form of a clamp having through slots on branches to accommodate threaded rods. The clamp is coupled by a threaded connection to an adjusting screw having a handle on one of its ends and a separable adapter that is provided with parallel grooves and mounted on a frame at its other end (see, e.g., USSR Inventor's Certificate N 1806660 A61, 1993).

A disadvantage of this apparatus is its low reliability. The repositioning mechanism is a two-arm lever mounted on a central support—an adapter. Sliders with bars, when the apparatus is installed, are disposed with a shift with respect to the central axis, which circumstance, when the adjusting screw is rotated, results in eccentric loads and the seizure effect.

The most similar technical solution is the apparatus for transosseous osteosynthesis, comprising two strips having longitudinal slots, at least three sliders having radial openings disposed in grooves in bracing frames, which frames have openings and are positioned between the strips, at least three bars having a threaded portion on their ends, intended for fixing the bone fragments and disposed in the radial openings of the sliders, three tightening bolts, according to the number of frames, which bolts extend through the slots of the strips and through the openings in the bracing frames, and are intended for compressing and fixing the bracing frames relative to the strips (see, e.g., RU patent 2125417, 1997).

The aforesaid device provides fixation of the bars and enhances reliability in the course of repositioning and during union of the fracture.

However, the aforesaid device does not ensure tool-aided axial compression and distraction of bone fragments. Furthermore, a disadvantage of this device is the highly complicated closed repositioning, because the bone fragments are aligned manually through soft tissues.

SUMMARY OF THE INVENTION

The object at the base of the instant invention is to create an apparatus for transosseous osteosynthesis, wherein the presence of a detachable repositioning mechanism for axial compression and distraction of bone fragments, which mechanism eliminates the effect of seizure, will make it possible to improve the quality of the closed repositioning by compression and mechanical fixation of bone fragments, and at the same time will make it possible to simplify the repositioning process using a unit of manual alignment of bone fragments, i.e. improve reliability of the apparatus, accelerate bone union and also, if necessary, lengthen bone tissue.

This object is accomplished in an apparatus for transosseous osteosynthesis, comprising two strips having longitudinal slots, at least three sliders having radial openings, which sliders are disposed in grooves in bracing frames having openings and positioned between the strips, at least three bars having a threaded portion at their ends, intended for fixation of bone fragments and disposed in the radial openings of the sliders, three tightening bolts according to the number of frames, which bolts extend through the strips' slots and through the openings in the bracing frames, and are intended for compression and fixation of the bracing frames relative to the strips, in that according to the invention, the apparatus further comprises a detachable repositioning mechanism for axial compression and distraction of the bone fragments, which mechanism has a bracing element positioned between the strips' ends, at least two guiding bars symmetrically secured in the bracing element, a mobile traverse mounted on the guiding bars and having a screw orifice, a lead screw secured in the bracing element whose geometric axis is parallel to the guiding bars' axes and whose threaded portion interacts with the mobile traverse screw orifice, at least two holders positioned on tightening bolts, two side bars to move the bracing frames, one end of each of the side bars being fixed to the mobile traverse, and the other end secured on a holder by means of a screw clamp.

It is advisable that each holder comprise a hollow body having an inner cylindrical surface, whose axis coincides with that of a corresponding tightening bolt, and a stem on the side surface of the body with an opening, which stem has a threaded portion, washers according to the number of holders and positioned under the head and under the nut of a corresponding tightening bolt, the washers contacting the holder body's inner cylindrical surface and intended for fixing the holder relative to the tightening bolt, a latch disposed in the holder body and intended for fixing the holder in the direction of axial movement along the tightening bolt.

It is useful that each holder be made in the form of a stepped pin whose axis is shifted relative to that of the tightening bolt, the pin having three steps, the first step comprising a head with an opening to accommodate a tightening bolt, the second step being provided with a radial opening to accommodate a side bar, the third step being provided with a thread to clamp the side bar, the apparatus comprising a bushing disposed on the second step of the pin, which bushing has two opposite radial recesses to accommodate the side bars, the outline of the recesses replicates the side bar outline.

It is advantageous that the lead screw comprise a vernier head.

It is also useful that the apparatus comprise at least one assembly for manual alignment of bone fragments, which assembly has a block with a T-shaped groove, a cylindrical clamping element made in the form of two semicylinders disposed with a gap and interconnected by means of a resilient element, the cylindrical clamping element having a radial cylindrical opening whose axis lies in the gap plane, which radial cylindrical opening is intended to accommodate a bar therein for fixation of the bone fragments, and also having a rectangular opening whose axis is perpendicular to the axis of the cylindrical opening, a screw with a nut, the central portion of the screw having a rectangular bulge with a slot, the head of the screw being disposed in the T-shaped groove of the block, the bulge being disposed in the rectangular opening of the cylindrical clamping element that has a gap, two washers encompassing the cylindrical clamping element from two sides, one of which washers contacting the block, the other washer contacting the nut.

It is advisable that the apparatus comprise an assembly for drawing in and fixing the bone fragments, which assembly is disposed between the strips provided with the longitudinal slots and has a bracing frame with two openings, a tightening bolt extending through the openings in the frame and through the grooves in the strips to secure the bracing frame, a needle having a bulge to draw a bone fragment into a fracture by means of a traction mechanism, which mechanism comprises a turret disposed in the bracing frame and having an annular projection and two mutually perpendicular openings, one of which openings is coaxial with the annular projection, a traction screw extending through the turret opening coaxial with the annular projection and having a head and a longitudinal groove to accommodate the needle therein, a check pin disposed in the traction screw head to fix the needle in a predetermined position in the traction screw, a nut disposed on the annular projection of the turret and interacting with the traction screw by its threaded portion, a bushing with a bead having a thread on the outer surface, which bushing is disposed in the second opening of the turret, a pin also disposed in the second opening of the turret and having a threaded shank disposed in the bushing with the bead, and a radial opening accommodating the traction screw, the longitudinal groove of which traction screw has a key positioned therein to prevent turning, a nut disposed in the beaded bushing and intended to prevent longitudinal movement of the turret relative to the frame, a second nut disposed on the threaded shank of the pin and intended to prevent turning of the turret relative to the frame.

It is advisable that the two strips, at least three bracing frames and the block having the T-shaped groove preferably be made of a material that is permeable to X-radiation.

It is advantageous that a thermosetting composite material including a carbon fibrous filler be used as the material permeable to X-radiation.

It is also useful that the material permeable to X-radiation have a bending strength of at least 500 MPa.

BRIEF DESCRIPTION OF THE DRAWING

The invention hereinafter is explained by a description of its preferable embodiments, with reference to the accompanying drawings, wherein:

FIG. 9 show a cross section taken along line XI—XI of FIG. 7, according to the invention;

FIG. 10 shows a cross section taken along line X—X of FIG. 9, according to the invention.

DESCRIPTION OF THE PREFERRED EMBODIMENTS

Figure 1:
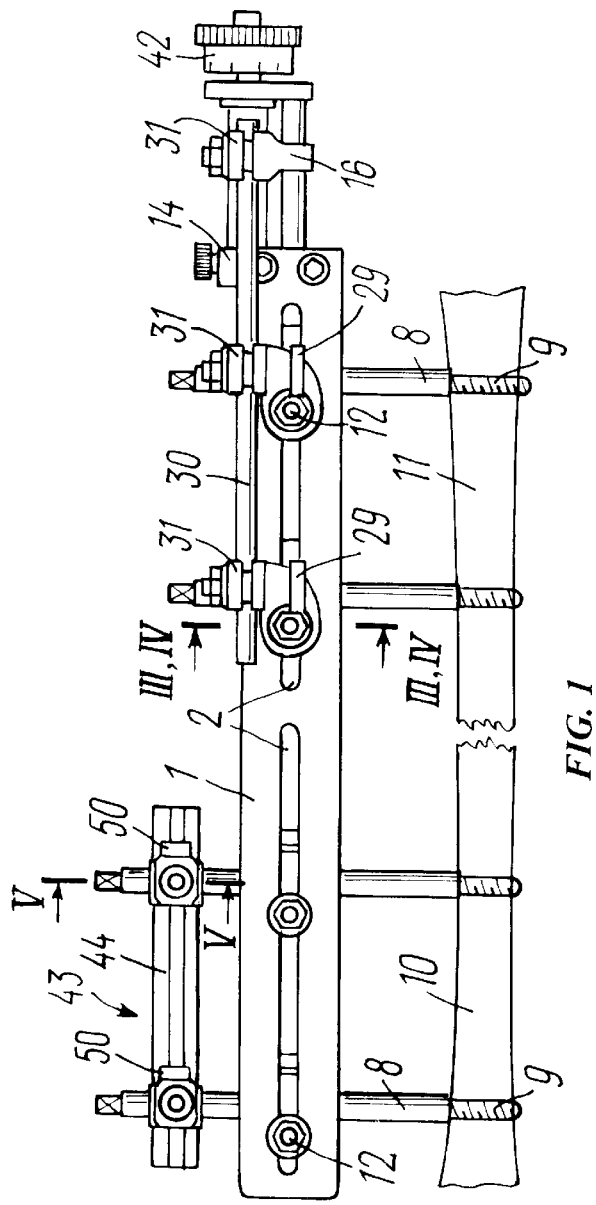
FIG. 1 shows a transosseous osteosynthesis device (front view), according to the invention.
Figure 2:
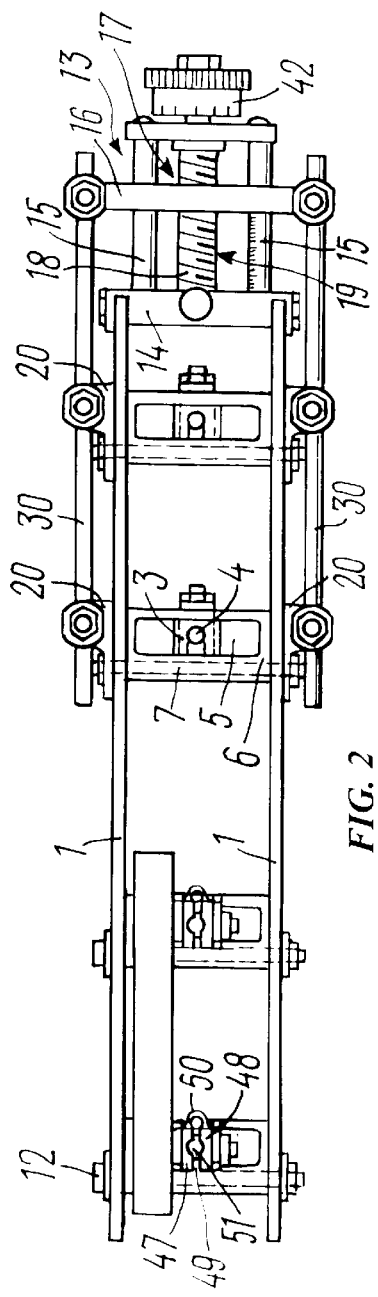
FIG. 2 shows a transosseous osteosynthesis device (top view), according to the invention.

The transosseous osteosynthesis apparatus comprises two strips 1 (FIG. 1), having longitudinal slots 2, and at least three sliders 3 (FIG. 2) having radial openings 4. The sliders 3 are disposed in grooves 5 in bracing frames 6 having openings 7 and positioned between the strips 1. FIGS. 1 and 2 show the embodiment wherein the apparatus comprises four sliders 3.

The apparatus comprises at least three bars 8 (FIG. 1). In the embodiment being described, the apparatus comprises four bars 8 in accordance with the number of sliders 3, which bars have a threaded portion 9 at their ends, are intended for fixation of bone fragments 10, 11 and are disposed in the radial openings 4 of the sliders 3.

The apparatus in the embodiment being described comprises four tightening bolts 12 in accordance with the number of frames, the bolts extending through the slots 2 of the strips 1 and the openings 7 in the bracing frames 6. The tightening bolts 12 are intended for compression and fixation of the bracing frames 6 relative to the strips 1.

The apparatus further comprises a detachable repositioning mechanism 13 for axial compression and distraction of bone fragments 10, 11, which mechanism comprises a bracing element 14 (FIG. 2) positioned between the ends of the strips 1.

The repositioning mechanism 13 comprises at least two guiding bars 15 symmetrically secured in the bracing element 14, a mobile traverse 16 positioned on the guiding bars 15. The mobile traverse 16 has a screw orifice 17.

The repositioning mechanism 13 comprises a lead screw 18 positioned in the bracing element 14 whose geometric axis is parallel to the axes of the guiding bars 15 and whose threaded portion 19 interacts with the screw orifice 17 of the mobile traverse 16.

In the embodiment being described, the repositioning mechanism 13 comprises four holders 20 (FIG. 2) mounted on tightening bolts 12.

Figure 3:
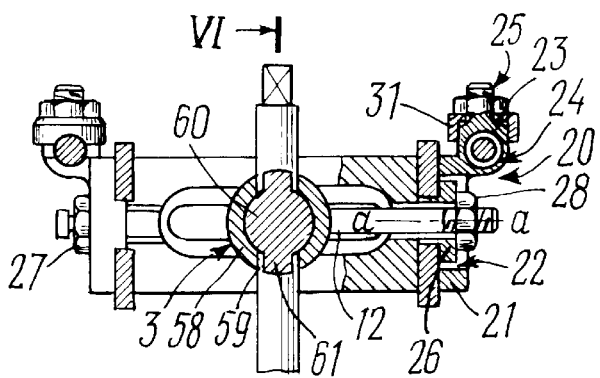
FIG. 3 shows a cross section taken along line III—III of FIG. 1, according to the invention.

Each of the holders 20 (FIG. 3) comprises a hollow body 21 having an inner cylindrical surface 22, whose "a—a" axis coincides with the axis of a corresponding tightening bolt 12. The holder also comprises a stem 23, which is disposed on the side surface of the body 21, having an opening 24, and has a portion with a thread 25.

The repositioning mechanism 13 comprises washers 26 in accordance with the number of holders 20, which washers are positioned under a head 27 and under a nut 28 of a corresponding tightening bolt 12. The washers 26 contact the inner cylindrical surface 22 of the body 21 of the holder and are intended for fixation of a holder 20 relative to a tightening bolt 12.

A holder 20 also comprises a latch 29 (FIG. 1) disposed in a body 21 of the holder and intended for fixation of the holder 20 in the direction of axial movement along a tightening bolt 12.

The repositioning mechanism 13 also comprises two side bars 30 (FIGS. 1, 2) for moving the bracing frames 6. One end of each side bar 30 is secured in the mobile traverse 16, and the other end is secured on the holder 20 using a clamp 31.

Figure 4:
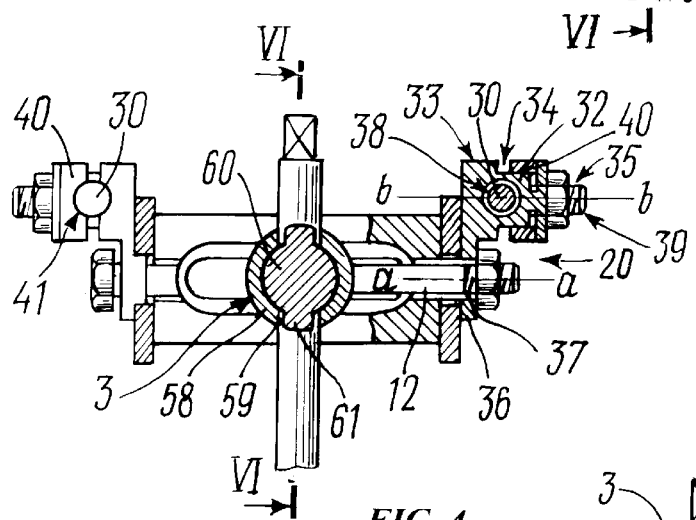
FIG. 4 shows a cross section taken along line IV—IV of FIG. 1, according to the invention.

According to the second embodiment, each holder 20 (FIG. 4) is made in the form of a stepped pin 32, whose "b—b" axis is shifted with respect to the axis "a—a" of the tightening bolt 12 and has three steps 33, 34, 35. The first step 33 comprises a head 36 having an opening 37 for accommodating a tightening bolt 12. The second step 34 is provided with a radial opening 38 to accommodate a side bar 30, and the third step 35 is provided with a thread 39 to clamp a side bar 30.

The apparatus comprises a bushing 40 disposed on the second step 34 of the pin, which bushing is provided with two opposite radial recesses 41 to accommodate the side bars therein, the outline of the recesses replicating the outline of a side bar 30.

The lead screw 18 (FIGS. 1, 2) comprises a vernier head 42 for rotating the lead screw to a predetermined angle.

Figure 5:
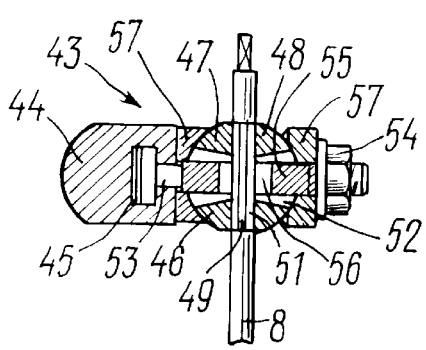
FIG. 5 shows a cross section taken along line V—V of FIG. 1, according to the invention.

The apparatus also comprises at least one assembly 43 (FIG. 1) for manual alignment of bone fragments 10, 11, which assembly has a block 44 (FIG. 5) provided with a T-shaped groove 45, the block being made of a material permeable to X-radiation, and has a cylindrical clamping element 46 made in the form of two semicylinders 47, 48 disposed with a gap 49 and interconnected by means of a resilient element 50 (shown in FIGS. 1, 2).

The cylindrical clamping element 46 (FIG. 5) is provided with a radial cylindrical opening 51 whose axis lies in the gap plane, which opening is intended for accommodating the bar 8 for fixation of bone fragments, and is provided with a rectangular opening 52 whose axis is perpendicular to the axis of the cylindrical opening 51.

The assembly 43 also comprises a screw 53 having a nut 54, the central portion of the screw 53 being provided with a rectangular bulge 55 having a slot 56. The head of the screw 53 is disposed in the T-shaped groove 45 of the block 44, and the bulge 55 is disposed in the rectangular opening 52 of the cylindrical clamping member 46 with the gap.

Two washers 57 encompass the cylindrical clamping element 46 from two sides, one of the washers contacting the block 44, the other washer contacting the nut 54.

Figure 6:
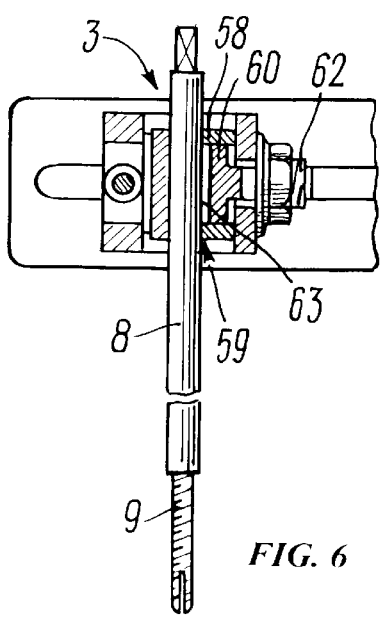
FIG. 6 shows a cross section taken along line VI—VI of FIG. 3 or 4, according to the invention.

In the described embodiments, each of the sliders 3 (FIG. 3, 4) is made in the form of a bushing 58 having grooves 59, and in which bushing a pin 60 having projections 61 and a threaded shank 62 is disposed (FIG. 6). The projections 61 match the grooves 59. The opening 4 in the slider 3 is formed by grooves 59 on the bushing 58 and by a radial opening 63 and projections 61 on the pin 60.

Figure 7:
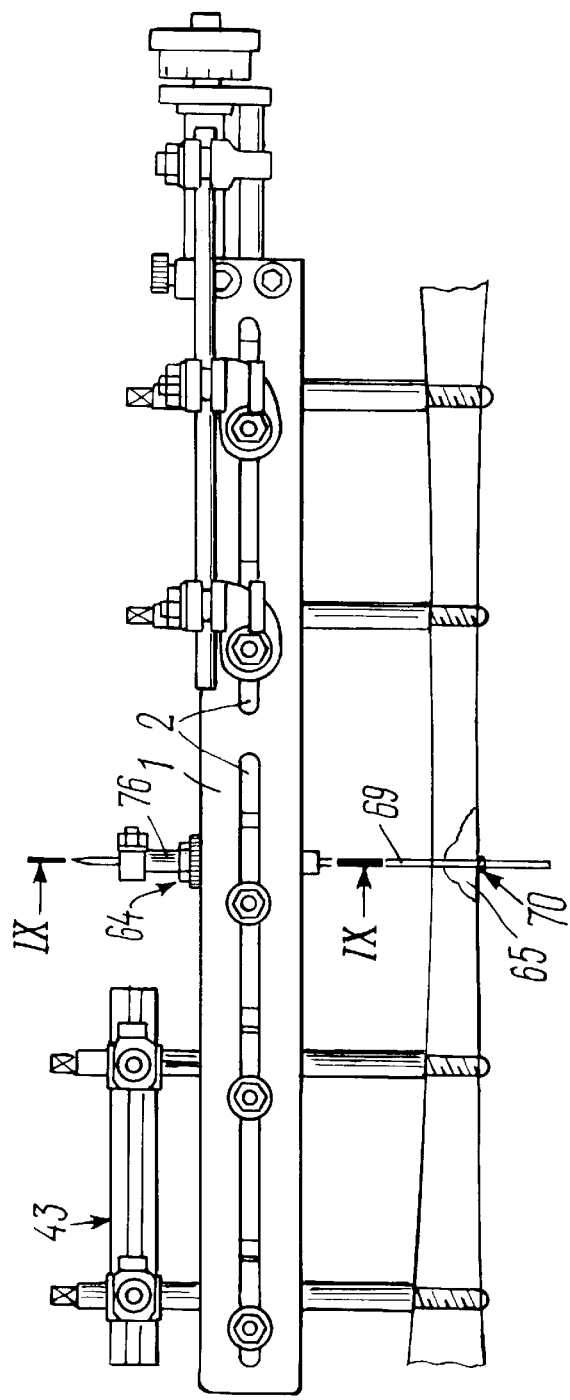
FIG. 7 shows a second embodiment of a transosseous osteosynthesis device (front view), according to the invention.
Figure 8:
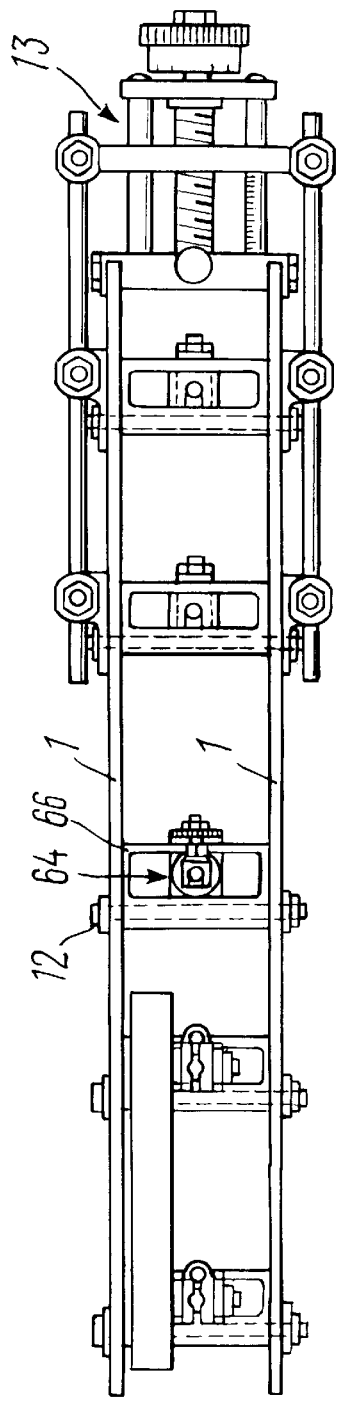
FIG. 8 shows the second embodiment of the transosseous osteosynthesis device (top view), according to the invention.

The apparatus also comprises an assembly 64 (FIGS. 7, 8) for drawing in and fixing bone fragments 65, which assembly is disposed between the strips 1 with longitudinal slots 2. The assembly 64 (FIGS. 9, 10) comprises a bracing frame 66 having two openings 67, 68, a tightening bolt 12 that extends through the openings 67, 68 in the frame and through the grooves 2 in the strips 1 to fasten the bracing frame 66.

The assembly 64 also comprises a needle 69 having a bulge 70 for drawing a bone fragment 65 into a fracture by means of a traction mechanism 71, which mechanism comprises a turret 72, disposed in the bracing frame 66. The turret 72 has an annular projection 73 and two mutually perpendicular openings 74, 75, one of which is coaxial with the annular projection 73. A traction screw 76 extends through the opening 74 in the turret 72, which opening is coaxial with the annular projection 73, and has a head 77 and a longitudinal groove 78 for accommodating the needle 69 therein. A check pin 79 is disposed in the head 77 of the traction screw for fixation of the needle 69 in a predetermined position in the traction screw 76.

A nut 80 is disposed on the annular projection 73 of the turret 72 and interacts by its threaded portion with the traction screw 76. A bushing 81, having a bead 82 with a thread 83 on the outer surface, is disposed in the opening 75 of the turret 72. A pin 84 is also disposed in the opening 75 of the turret 72 and has a threaded shank 85 disposed in the bushing 81. The pin 84 has a radial opening 86 that accommodates the traction screw 76, in the longitudinal groove 78 of which a screw key 87 is positioned to prevent turning.

A nut 88 is disposed on the bushing 81 having a bead and is intended for prevention of longitudinal movement of the turret 72 relative to the frame 66. A second nut 89 is disposed on the threaded shank 85 of the pin 84 and is intended for prevention of the turret 72 turning relative to the frame 66.

In the described embodiments, the strips 1, bracing frames 6, 66, block 44 having a T-shaped groove are made of a material that is permeable to X-radiation.

A thermosetting composite material including a carbon fibrous filler is used as the material permeable to X-radiation.

The material permeable to X-radiation has a bending strength of at least 500 MPa.

The apparatus for transosseous osteosynthesis operates as follows.

The bars 8 are taken out of the apparatus (FIG. 1), and via the threaded portion 9 the bars are screwed into bone fragments 10 and 11. The nuts on all the tightening bolts 12 and on the clamps 31 of the holders 20 are slackened. The apparatus for transosseous osteosynthesis is positioned on the injured limb, the openings 4 of each of the sliders 3 are registered in turn with a corresponding bar 8. Wherewith the strips 1 are arranged along the patient's limb at the required distance therefrom for dressing. The bars 8 of the bone fragment 11 are fixed by tightening the nuts on corresponding sliders 3.

The assembly 43 is positioned on the bars 8 of the bone fragment 10. For that purpose, the openings 51 of each of the clamping elements 46 are aligned in turn with a respective bar 8. The block 44 is disposed in parallel with the axis of the bone fragment 10 at a distance from the strips 1, which is sufficient so that a surgeon will be able to hold the block 44 with his hand. The nuts 54 are tightened, whereby the bars 8 are compressed by the semicylinders 47 and 48 and are fixed relative to the block 44.

By manual movement of the assembly 43 relative to the strips 1, the axis of the bone fragment 10 is aligned with the axis of the bone fragment 11, and the fracture is compared. Wherewith, the freely-moving frames 6 along the grooves 2 on the strips 1 and the sliders 3 along the grooves 5 in the frames 6 do not hinder the repositioning that is being carried out.

The strips 1, frames 6 and block 44, being permeable to X-radiation, do not shade the fracture region during radiology monitoring of the closed repositioning of the bone fractures. The bars 8 of the bone fragment 10 are fixed by tightening the nuts on the sliders 3 and on the tightening bolts 12. Wherewith, the nuts 28 on the tightening bolts that are registered with the holders 20 remained slackened. The traverse 16 is set in the initial position by rotation of the lead screw 18 through the vernier head 42.

For subsequent distraction of bone fragments 10 and 11, the traverse 16 is positioned near the bracing element 14, and for compression —near the vernier head 42. The nuts of the clamp 31 are tightened, and the position of the side bars 30 is fixed relative to the holders 20. By rotation of the vernier head 42 to a required angle, distraction or compression of bone fragments 10 and 11 is performed. Wherewith, the bracing frames 6 with the sliders 3, in which the bars 8 of bone fragment 11 are fixed, move along the grooves 2 in the strips 1 to the value corresponding to the turn angle of the scale of the vernier head 42. The nuts 28 on the tightening bolts 12, that correspond to the frames 6 and the bars 8 of the bone fragment 11, are tightened.

In the case of a splintered fracture (FIG. 7), after the bars 8 have been screwed into bone fragments 10, 11, the bone fragment 65 is drilled by the sharp point of the needle 69 at the side opposite to the projecting bars, and the needle 69 is pushed to the side of the projecting bars. The needle 69 impales the assembly 64 for drawing-in and fixing the fragment 65, and the assembly 64 is disposed between the strips 1, and the tightening bolt 12 is installed.

The position of the traction mechanism 71 is corrected by moving it along the bracing frame 66 and stopped by tightening the nut 88. The needle 69 is secured in the traction mechanism 71 by tightening the nut on the stop pin 79. The traction screw 76 with the needle 69 is moved by rotation of the nut 80, whereby the fragment 65 is drawn into the fracture. The position of the needle 69 is fixed by tightening the nut 89.

The repositioning mechanism 13 is taken off, wherefore the nuts of the clamps 31 on the holders 20 are slackened. The fastening bolts, that fasten the bracing element 14 to the ends of the strips 1, are removed, and the mechanism 13 is removed in the direction that is parallel to the axes of the side bars 30. The latches 29 on the holders 20 are turned, and the holders are taken off of the washers 26.

Removal of the apparatus without the repositioning mechanism 13 from a patient after treatment is done according to the following procedure. The nuts of all the sliders 3 and all the tightening bolts 12 are slackened. The strips 1 with frames 6 and sliders 3 are removed from the bars 8. All the bars 8 are withdrawn from the bone.

What is claimed is:

1. An apparatus for transosseous osteosynthesis, comprising:
   two strips having longitudinal slots,
   at least three sliders having radial openings disposed in grooves in bracing frames, which frames have openings and are positioned between the strips,
   at least three bars having a threaded portion at their ends, intended for fixation of bone fragments and disposed in the radial openings of the sliders,
   three tightening bolts according to the number of frames, which bolts extend through the strips' slots and through openings in the bracing frames and are intended for compressing and fixing the bracing frames relative to the strips,
   a detachable repositioning mechanism for axial compression and distraction of the bone fragments, and having:
   a bracing element positioned between ends of the strips,
   at least two guiding bars symmetrically secured in the bracing element,
   a mobile traverse positioned on the guiding bars and having a screw orifice,
   a lead screw secured in the bracing element whose geometric axis is parallel to axes of the guiding bars and whose threaded portion interacts with the threaded portion of the mobile traverse,
   at least two holders positioned on the tightening bolts,
   two side bars for moving the bracing frames, one end of each of the frames being secured on the mobile traverse, and the other end being secured on a holder by means of a screw clamp.

2. The apparatus as claimed in claim 1, wherein each holder comprises:
   a hollow body having an inner cylindrical surface, whose axis coincides with that of a corresponding tightening bolt, and a stem on the side surface of the body with an opening, which stem has a threaded portion;
   washers according to the number of holders, the washers positioned under the head and under the nut of a corresponding tightening bolt, the washers contacting the holder body's inner cylindrical surface and intended for fixing the holder relative to the tightening bolt;
   a latch disposed in the holder body and intended for fixing the holder in the direction of axial movement along the tightening bolt.

3. The apparatus as claimed in claim 1, in which each holder is made in the form of a stepped pin whose axis is shifted relative to that of the tightening bolt, said pin having three steps, the first step comprising a head with an opening to accommodate a tightening bolt, the second step being provided with a radial opening to accommodate a side bar, the third step being provided with a thread to clamp the side bar;
   the apparatus further comprises a bushing disposed on the second step of the pin, which bushing has two opposite radial recesses to accommodate the side bars, the outline of the recesses replicates the side bar outline.

4. The apparatus as claimed in claim 1, in which the lead screw comprises a vernier head.

5. The apparatus as claimed in claim 1, in which said device comprises:
   at least one assembly for manual alignment of bone fragments, which assembly has:
   a block with a T-shaped groove,
   a cylindrical clamping element in the form of two semi-cylinders disposed with a gap and interconnected by means of a resilient element;
   the cylindrical clamping element having a radial cylindrical opening whose axis lies in the gap plane, which radial cylindrical opening is intended to accommodate a bar for fixation of the bone fragments, and also having a rectangular opening whose axis is perpendicular to the axis of the cylindrical opening;
   a screw with a nut, the central portion of said screw having a rectangular bulge with a slot, the head of said screw being disposed in the T-shaped groove of the block, and the bulge being disposed in the rectangular opening of the cylindrical clamping member that has a gap;
   two washers encompassing the cylindrical clamping element from two sides, one of which washers contacting the block, the other washer contacting the nut.

6. The apparatus as claimed in claim 1, in which the apparatus further comprises:
   an assembly for drawing-in and fixing the bone fragments, which assembly is disposed between the strips provided with the longitudinal slots, and has:
   a bracing frame with two openings,
   a tightening bolt extending through the openings in the frame and through grooves in the strips to secure the bracing frame;
   a needle having a bulge to draw a bone fragment into a fracture by means of a traction mechanism, which mechanism comprises a turret disposed in the bracing frame and having an annular projection and two mutually perpendicular openings, one of which openings is coaxial with the annular projections, a traction screw extending through the turret opening coaxial with the annular projection and having a head and a longitudinal groove to accommodate the needle therein, a check pin disposed in the traction screw head to fix the needle in a predetermined position in the traction screw;

a nut disposed on the annular projection of the turret and interacting with the traction screw by its threaded portion;

a bushing with a bead having a thread on the outer surface, which bushing is disposed in the turret's second opening;

a pin also disposed in the turret's second opening and having a threaded shank disposed in the bushing having said bead, and a radial opening accommodating the traction screw, the longitudinal groove of which traction screw has a key positioned therein to prevent turning;

a nut disposed in the beaded bushing and intended to prevent longitudinal movement of the turret relative to a frame;

a second nut disposed on the threaded shank of the pin and intended to prevent turning of the turret relative to the frame.

7. The apparatus as claimed in claim 1, in which two strips, at least three bracing frames and the block having the T-shaped groove are made of a material that is permeable to X-radiation.

8. The apparatus as claimed in claim 7, in which a thermosetting composite material including a carbon fibrous filler is used as material permeable to the X-radiation.

9. The apparatus as claimed in claim 7, in which the material permeable to X-radiation has a bending strength of at least 500 MPa.

* * * * *